(12) United States Patent
Wiley et al.

(10) Patent No.: US 6,245,712 B1
(45) Date of Patent: Jun. 12, 2001

(54) CHEMICAL PINCHING METHOD AND COMPOSITION

(75) Inventors: Robert P. Wiley, Pershore; Maria J. McKelvie, Evesham, both of (GB); Bruno Folchi, Latina (IT)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 09/403,482

(22) PCT Filed: May 13, 1998

(86) PCT No.: PCT/US98/09731

§ 371 Date: Oct. 21, 1999

§ 102(e) Date: Oct. 21, 1999

(87) PCT Pub. No.: WO98/51148

PCT Pub. Date: Nov. 19, 1998

(51) Int. Cl.[7] .......................... A01N 43/00; A01N 31/00; A01N 31/04; A01N 31/06

(52) U.S. Cl. .............................................................. 504/185

(58) Field of Search ................................... 504/184, 185, 504/351

(56) References Cited

U.S. PATENT DOCUMENTS 5,424,272 * 6/1995 Chang .................................. 504/184

FOREIGN PATENT DOCUMENTS

1502757 * 3/1978 (GB) .

* cited by examiner

Primary Examiner—S. Mark Clardy
Assistant Examiner—Alton Pryor
(74) Attorney, Agent, or Firm—Raymond D. Thompson

(57) ABSTRACT

A method of inhibiting the growth of suckers in tobacco plants which comprises applying to said tobacco plants after topping an effective amount of a composition comprising saturated fatty alcohols and polyoxyethylene sorbitan esters.

9 Claims, No Drawings

CHEMICAL PINCHING METHOD AND COMPOSITION

This application is a 371 of PCT/US 98/09731 filed May 13, 1998.

BACKGROUND

Suckers in Virginia tobacco are chemically controlled by using two main types of substances: contacts (fatty alcohols, such as n-decanol) and systemics, such as maleic hydrazide (MH).

Fatty alcohols are generally very effective in killing small suckers, but they are characterized by a disgusting smell, which can be very annoying for farmers during the distribution on the cultivars, causing nausea, vomiting, suspension of work, etc. Furthermore people living in the surrounding areas may complain about the smell and limit the tobacco producer's ability to use this valuable chemical pinching agent in cultivation of his tobacco.

To overcome this problem new formulations have been developed containing n-decanol and a specialized polyoxyethylene sorbitan monooleate. These new formulations are effective at reducing odor without altering their biological activity and above all, without causing any negative side-effect on the characteristics of flue-cured tobacco leaves, which might be detrimental for cigarette manufacture. Attempts have surprisingly not been successful directed to modifying the n-decanol formulations to contain some flavoring substances which are supposed to mask the smell of fatty alcohols.

SUMMARY OF THE INVENTION

One aspect of this invention is a method of inhibiting the growth of suckers in tobacco plants which comprises applying to said tobacco plants after topping an effective amount for inhibiting tobacco sucker growth of an aqueous solution containing as active ingredient from about 10% to about 90% by weight of a saturated $C_6$ to $C_{18}$ fatty alcohol and about 90% to about 10% of polyoxyethylene sorbitan ester comprising a mixture of mono, di and triesters.

Another aspect of this invention is disclosed wherein said polyoxyethylene sorbitan ester comprises a polyoxyethylene sorbitan ester having the formula

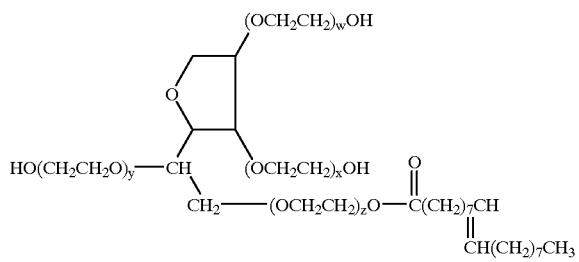

wherein w+x+y+z is between 6 and 25.

Another aspect of this invention is disclosed wherein said fatty alcohol is N-decanol.

Another aspect of this invention is disclosed wherein said fatty alcohol is N-octanol.

Another aspect of this invention is disclosed wherein said fatty alcohol constituent comprises a mixture consisting essentially of N-octanol and N-decanol.

Another aspect of this invention is disclosed wherein w+x+y+z is between 14 and 22

Another aspect of this invention is disclosed wherein w+x+y+z is between 16 and 20

Another aspect of this invention is disclosed wherein said polyoxyethylene sorbitan ester is a condensation reaction product of ethylene oxide and sorbitan fatty acids wherein the fatty acids are reacted in molar excess of from 6 to 25 moles per mole of ethylene oxide.

Another aspect of this invention is disclosed wherein said solution includes an emulsifying agent, wetting agent, spreaders, solubilizers, stickers, foam suppressors and drift control agents.

Another aspect of this invention is disclosed liquid composition for inhibiting the growth of tobacco suckers comprising an effective amount for inhibiting tobacco sucker growth of an aqueous solution containing as active ingredient from about 10% to about 90% by weight of a saturated $C_6$ to $C_{18}$ fatty alcohol and about 90% to about 10% of polyoxyethylene sorbitan ester comprising a mixture of mono, di and triesters. Another aspect of this invention is disclosed wherein said saturated fatty alcohol comprises N-decanol. Another aspect of this invention is disclosed wherein said saturated fatty alcohol constituent comprises a mixture consisting essentially of N-octanol and N-decanol. Another aspect of this invention is disclosed further including an emulsifying agent, wetting agent, spreaders, solubilizers, stickers, foam suppressors and drift control agents.

Another aspect of this invention is disclosed a liquid composition for inhibiting the growth of tobacco suckers as recited above further including a wetting agent.

Another aspect of this invention is disclosed further comprising the steps of sequentially and alternately contacting the crop buds with said aqueous solution and a growth regulator.

Another aspect of this invention is disclosed further comprising applying said aqueous solution selectively to the suckering zone. Another aspect of this invention is disclosed further comprising applying said aqueous solution at a rate of from about 0.3 to about 20 ml per cultivar.

Another aspect of this invention is a method for the inhibition of secondary growth in azaleas comprising applying topically an effective amount of the aqueous solution.

Another aspect of this invention is disclosed is the inhibition of plant growth by topical application of chemical agent to meristematic tissue, the improvement which comprises the utilization of an effective amount of a composition comprising as active ingredient from about 10% to about 90% by weight of a saturated $C_6$ to $C_{18}$ fatty alcohol and about 90% to about 10% of polyoxyethylene sorbitan ester having the structure

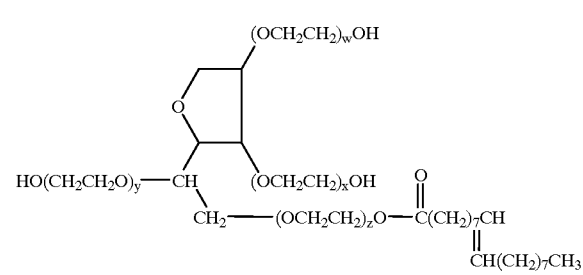

wherein w+x+y+z is between 6 and 25.

DETAILED DESCRIPTION OF THE INVENTION

The long chain fatty acid of this invention constitutes the active ingredient of the formulation for chemical suckering of tobacco but the critical factor in masking the objectionable odor of the fatty acid is the presence in the polyoxyethylene sorbitan ester of an Gas Chromatographic peak between 18.00 minutes and 19.00 minutes of column retention time. FIG. 1 shows the GC trace for the polyoxyethylene sorbitan ester of the control standard n-decanol formulation (20/80 weight ratio). FIG. 2 shows the polyoxyethylene sorbitan ester of this invention showing clearly second peak from the left having a retention time of 18.5 minutes is present but is not present in the polyoxyethylene sorbitan ester of the commercial control formulation which is Royaltac, a product of Uniroyal Chemical Company. This surprising result in decreasing odor in the applied formulation is believed to derive from the particular component of the polyoxyethylene sorbitan ester represented by this critical GC peak. In order to detect this peak any recognized analytic method may be utilized, but the following was used to generate the traces of FIG. 1 and FIG. 2.

Formulating Methods

A water-containing or aqueous emulsion, the most preferred embodiment of the invention, is prepared from a solution, as described below, into which a surface active agent has been added.

A suitable liquid solution is formed by dissolving the active ingredient, saturated $C_6$ to $C_{18}$ fatty alcohol in an aqueous or organic solvent. In most cases, the solvent which acts as the carrier, is an organic solvent.

Preferred solvents include aromatic hydrocarbons such as toluene and xylene. Additional solvents that are preferred include such organic compounds as acetone, methanol, isopropanol, tert-butyl alcohol, cyclohexanone, dioxane, dimethylformamide, dimethyl sulfoxide, ethylene dichloride, diacetone alcohol and N-methylpyrrolidone.

Surface active agents suitable for purposes of forming effective aqueous emulsions within the contemplation of our invention are known to those skilled in the art.

*McCutcheon's Detergents and Emulsifiers,* Allured Publishing Corp., Ridgewood, N.J. (1970); U.S. Pat. No. 2,514,916, at Columns 2 to 4; and U.S. Pat. No. 2,547,734, at Columns 3 and 4, for example, provide detailed examples of such surface active agents suitable for this purpose. As is indicated in these references, the surface active agent may be anionic, non-ionic or cationic.

In yet another embodiment of our present invention, our composition can take the form of an aerosol. In preparing this aerosol, we prefer to dissolve the compound of formula I in a first solvent.

The first solvent is conventional in the sense that it is not highly volatile. The resulting solution is then admixed with a second solvent that is highly volatile. The volatile second solvent is commonly called a "liquid aerosol carrier."

The aerosol carrier is liquid only under elevated pressure. At ambient temperature and pressure, namely 25 degrees Celsius and one (1) atmosphere pressure, such an aerosol carrier is typically a gas.

Other optional ingredients may also be desirable for particular applications including: emulsifying agent, wetting agent, spreaders, solubilizers, stickers, foam suppressors and drift control agents at effective levels, generally between 0.01 and 2 weight percent.

Gas Chromatographic Test Method

The following method was utilized to determine the presence critical component of the which occurs at 18.5+/−0.5 minutes as shown in FIG. 1 and FIG. 2.

The samples to be tested were weighed into 3 ml reactive vials and magnetic stirring fleas were added along with 1 ml of Silanization Reagent [BSA; TMCS; TMSI 3:2:3 [N,O-bis(trimethylsilyl)acetamide+Trimethylchlorosilane+N-trimethyl silylimidazole] was added. 1 ml of toluene was added to allow the sample and Reagent to mix and react. The samples were allowed to stir (while lightly capped to prevent excess air/humidity from entering and to allow pressure release) for 30–40 min. The samples were then quantitatively transferred with HPCC grade methylene chloride to clean labeled 10 ml volumetric flasks. The samples were then brought to the mark with additional methylene chloride. ($U_f$=10 ml) they were then sampled for GC analysis.

The above reaction conditions were the result of a first attempt at a much lower concentration of sample and longer reaction time.

Chromatograph for Analysis

Varian Model 3600

Column: 15M×0.53 mm ID 1.5 μm film DB-5+

Injector: Varian SPI on column @ 300° C., 0 min to 325° C. @ 15° C./min hold 65 min Oven:
  Initial: 60° C., 2 min
  Final 310° C., hold 40 min
  Rate 5° C./min Column flow 5 ml/min Helium make-up @ 35 ml/min Helium detector temp 320° C.

Tobacco Field Trials

In these experiments, the traditional formulation of n-decanol—called control formulation with the FIG. 1 GC curve—was compared with the formulation of this invention having FIG. 2 GC trace. Both formulations were 80/20 n-decanol to polyoxyethylene sorbitan ester. Two large scale field experiments were carried out, one in Central Italy referred to as Region 1 (results in Table 1) and the other in Northern Italy referred to as Region 2 (results in Table 2).

In order to have fragrance and efficacy evaluations, some trials were carried out on some large tobacco farms Regions 1 and 2, treating hundreds of hectares with the formulation of this invention and the control product without the specialized ingredient having the 18.5 minute GC peak of this invention.

Trial in Region 1

The trial in Region 1 was carried out on a silty-clay soil, with a pH of 7.9, organic matter content of 1.7% and low nitrogen content. Tobacco was grown following the normal farm practices in central Italy, as reported in Table 1. N-decanol for sucker control was applied as a water solution of the formulated products (4% v/v).

The Control formulation and the formulation of this invention were compared using a randomized block design, with four replications and a plot surface-area of 20 $m^2$.

Chemicals were sprayed by using a Plot Oxford Precision Sprayer, equipped with a single-row bar, fitted with three solid cone nozzles (TG1-TG3-TG1), delivering 600 1 $ha^{-1}$ spray solution at 100 kPa pressure. During the treatments, nozzles were kept 20 cm above the plants.

Biological activity was recorded by collecting all the apical suckers in each plot, counting and weighing them (fresh and dry weight). The average length of the suckers in each plot was also recorded. Tobacco leaves were harvested in three different times 20 days apart. At each harvesting time, leaves from each plot were separately weighed, combined over replications and cured in different barns, to avoid cross contamination. Flue-cured leaves were placed in separate polyethylene bags for each treatment and stored for cigarette smoke flavor evaluation.

Flue-cured leaves were evaluated for quality, by a technical commission composed of three experts from the state agency with responsibility. During this evaluation, the extrinsic characteristics of tobacco leaves (development, color, tissue texture, consistency, etc . . . ) were subjectively recorded and used to estimate the percentage of yield to be assigned to each of the three commercial grades A, B and C (A being the highest quality grade).

Trial in Region 2

The second trial was carried out on a sandy soil, following the normal farming practices for Northern Italy, with respect to the choice of the cultivar (K326), the date of transplanting (28.5.96), plant spacing (1.10×0.37 m), plot surface area (374 $m^2$). Biological activity was recorded.

Fragrance Evaluation

The acceptability of the smell of each formulation including the control formulation was assessed with respect to the currently used commercial formulation. In all the trials, subjective evaluations were made during the distribution, both by the operator and by other assistants. In both trials some technicians followed the sprayer during the applications and recorded the smell on a scale from 0 to 100 (in terms of intensity, acceptability, persistence and diffusion).

Results

Biological Activity

In the trial in central Italy, both formulations gave a good control of apical suckers, with no significant differences among them.

Acceptability of the Smell

Results obtained in Region 1 are summarized in Table 1. In all the cases and regardless of the formulation, a prolonged exposure to the smell of Control formulation resulted in some nuisance for all the people involved in the experiments. The flavor of the formulation of this invention proved to be characterized by a high intensity at the treatment and two hours later, but it was considered, due to its "neutral" smell, more acceptable than the commercial one.

TABLE 1

|  | At the treatment | 2 hours later | 8 hours later | 24 hours later |
|---|---|---|---|---|
| Formulation | A I | I | I | I |
| Ex. 1-invention | 50  80 | 60 | 20 | 20 |
| Control formulation | 0  100 | 70 | 40 | 20 |

Footnotes to Table:
I = intensity of smell. The I scale = 0–100 with [0 = zero intensity 10 = high intensity.
A = acceptability of smell. The A scale = 0–100 with [0 = unpleasant 10 = acceptable.
*Number of replication of readings that support these averages is 5 persons The Example 1—the formulation of the invention, was considered to be much more acceptable than the commercial formulation for its smell and low intensity and persistence.

TABLE 2

|  | Smell at the treatment | 6 hours later | 24 hours later |
|---|---|---|---|
| Formulation | A I | I | I |
| Ex. 1-invention | 60  20 | 0 | 0 |
| Control formulation | 0  100 | 0 | 0 |

Footnotes to Table:
I = intensity of smell. The scale = 0–100 with [0 = zero intensity 10 = high intensity.
A = acceptability of smell. The scale = 0–100 with [0 = unpleasant 10 = acceptable.
*Number of replication of readings that support these averages is 5 persons All the trials in these two years showed that the new formulations of this invention's formulation are as effective as the currently used one in controlling suckers in tobacco. Furthermore the abovementioned formulations did not negatively influence the qualitative and quantitative characteristics of flue-cured tobacco.

Concerning the smell of fatty-alcohols, the formulation of this invention proved to be more acceptable than the standard formulations. Example 1, the formulation of the invention, proved to have a less intense smell compared to the Control formulation and thus was more acceptable for the operators working on the two experimental farms, for the farmers of the tobacco farms and for people living in the surrounding area. Because of its "neutral" smell, this formulation was considered the best one to solve the problem of the unpleasant smell of fatty alcohols both Regions 1 and 2, the biggest producers (90%) of Virginia tobacco in Italy.

What we claim is:

1. A method of inhibiting the growth of suckers in tobacco plants which comprises applying to said tobacco plants after topping an effective amount for inhibiting tobacco sucker growth of an aqueous solution containing as active ingredient from about 10% to about 90% by weight of a saturated $C_6$ to $C_{18}$ fatty alcohol and about 90% to about 10% of polyoxyethylene sorbitan ester comprising a mixture of mono, di and triesters including a polyoxyethylene sorbitan ester having the formula $$HO(CH_2CH_2O)_y-CH \quad (OCH_2CH_2)_wOH \quad (OCH_2CH_2)_xOH$$
$$\underset{H_2}{C}-(OCH_2CH_2)_zO-C \overset{O}{\underset{(CH_2)_7}{\diagdown}}$$
$$HC$$
$$\parallel$$
$$C-(CH_2)_7CH_3$$
$$H$$

wherein w+x+y+z is between 6 and 25.

2. The method of claim 1 wherein said fatty alcohol is selected from the group consisting of N-decanol, N-octanol and mixtures of N-octanol and N-decanol.

3. The method of claim 1 wherein w+x+y+z is between 14 and 22.

4. The method of claim 1 wherein said polyoxyethylene sorbitan ester mixture comprises a condensation reaction product of ethylene oxide and sorbitan fatty acids wherein the fatty acids are reacted in molar excess of from 6 to 25 moles per mole of ethylene oxide.

5. The method of claim 1 wherein said solution further comprises optional ingredients selected from the group consisting of emulsifying agent, wetting agent, spreaders, solubilizers, stickers, foam suppressors and drift control agents.

6. A method as in claim 1 further comprising the steps of sequentially and alternately contacting the plant buds with said aqueous solution and a growth regulator.

7. A method as in claim 1 further comprising applying said aqueous solution selectively to suckering zone at a rate of from about 0.3 to about 20 ml per cultivar.

8. In the inhibition of plant growth by topical application of chemical agent to meristematic tissue, the improvement which comprises topically applying to meristematic tissue an effective amount of a composition comprising as active ingredient from about 10% to about 90% by weight of a saturated $C_6$ to $C_{18}$ fatty alcohol and about 90% to about 10% of polyoxyethylene sorbitan ester comprising a mixture of mono, di and triesters including a polyoxyethylene sorbitan ester having the formula

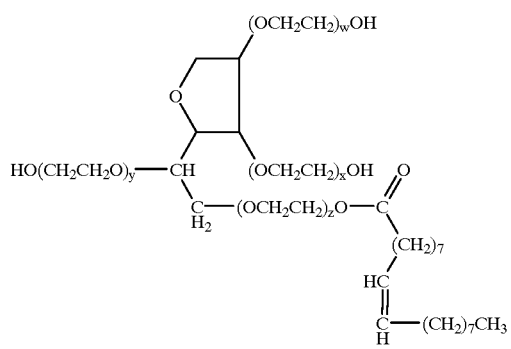

wherein w+x+y+z is between 6 and 25.

9. A liquid composition for inhibiting the growth of tobacco suckers comprising an effective amount for inhibiting tobacco sucker growth of an aqueous solution containing as active ingredient from about 10% to about 90% by weight of a saturated $C_6$ to $C_{18}$ fatty alcohol and about 90% to about 10% of polyoxyethylene sorbitan ester comprising a mixture of mono, di and triesters including a polyoxyethylene sorbitan ester having the formula

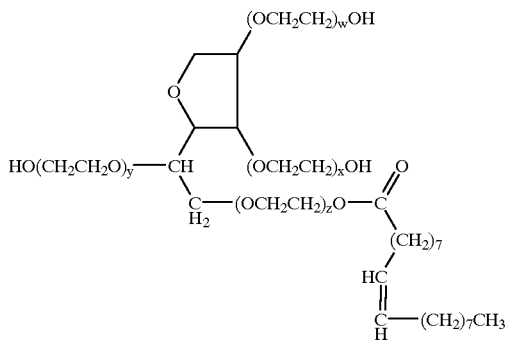

wherein w+x+y+z is between 6 and 25.

* * * * *